United States Patent [19]
Fujiyama et al.

[11] 4,368,336
[45] Jan. 11, 1983

[54] PROCESS FOR FORMYLATING XYLENE MIXTURE

[75] Inventors: Susumu Fujiyama; Shunichi Matsumoto; Yuji Takamizawa, all of Kurashika, Japan

[73] Assignee: Mitsubishi Gas Chemical Company, Inc., Tokyo, Japan

[21] Appl. No.: 233,304

[22] Filed: Feb. 11, 1981

[30] Foreign Application Priority Data

Feb. 14, 1980 [JP] Japan .................................. 55/16785

[51] Int. Cl.³ ............................................. C07C 45/49
[52] U.S. Cl. ................................................. 568/428
[58] Field of Search .......................................... 568/428

[56] References Cited
U.S. PATENT DOCUMENTS
2,485,237 10/1949 Gresham et al. ................... 568/428

Primary Examiner—Bernard Helfin
Attorney, Agent, or Firm—Armstrong, Nikaido, Marmelstein & Kubovcik

[57] ABSTRACT

A xylene mixture containing at least one of m-xylene and o-xylene is formylated by carbon monoxide in the presence of hydrogen fluoride and boron trifluoride at a molar ratio of boron trifluoride to sum total of m-xylene and o-xylene in the xylene mixture of not more than 1.5 to selectively and correspondingly produce at least one of 2,4-dimethylbenzaldehyde and 3,4-dimethylbenzaldehyde.

3 Claims, No Drawings

PROCESS FOR FORMYLATING XYLENE MIXTURE

This invention relates to a process for formylating a xylene mixture, and more particularly to a process for formylating a xylene mixture containing at least one of m-xylene and o-xylene among four xylene isomers, that is, ethylbenzene, o-xylene, m-xylene and p-xylene with carbon monoxide (CO) in the presence of hydrogen fluoride (HF) and boron trifluoride (BF$_3$) as a catalyst to selectively and correspondingly produce at least one of 2,4-dimethylbenzaldehyde and 3,4-dimethylbenzaldehyde. At the same time, a xylene mixture containing no m-xylene, or o-xylene, or both, or containing a very small amount of m-xylene, or o-xylene, or both can be obtained. The product dimethylbenzaldehydes are useful raw materials for synthesizing trimellitic acid.

Trimellitic acid is now prepared by oxidation of pseudocumene, but the raw material pseudocumene is somewhat in a short supply owing to a drastic increase in demand for the use in the field of heat-resistant plasticizer, etc.

Taking into account the production of trimellitic acid from the dimethylbenzaldehydes produced from the xylenes, which are supplied in a large amount at a low cost, the present inventors have made extensive studies of formylation of xylenes, and have established the present invention.

An object of the present invention is to provide a process for formylating a xylene mixture containing at least one of m-xylene and o-xylene by carbon monoxide in the presence of hydrogen fluoride and boron trifluoride as a catalyst, which comprises conducting formylation at a molar ratio of boron trifluoride to sum total of m-xylene and o-xylene in the xylene mixture of not more than 1.5, thereby selectively and correspondingly producing at least one of 2,4-dimethylbenzaldehyde and 3,4-dimethylbenzaldehyde.

Dimethylbenzaldehydes are considerably more advantageous in oxidation reactivity than pseudocumene, and 2,4-dimethylbenzaldehyde and 3,4-dimethylbenzaldehyde can be produced from m-xylene and o-xylene as the feed alkylbenzene, which are relatively amply available at low costs as raw materials for the dimethylbenzaldehydes for trimellitic acid.

In the present invention, a feed xylene mixture for separation of xylene isomers, or a xylene mixture in the intermediate step in a process for separating xylene isomers can be utilized as more advantageous feed xylene mixture. That is, the present invention has such an advantage that any xylene mixture, so far as it contains a considerable amount of m-xylene and/or o-xylene, can be used. Generally, four C$_8$ aromatic isomers, that is, ethylbenzene, o-xylene, m-xylene and p-xylene, are formylated by CO in the presence of HF-BF$_3$ to form p-ethylbenzaldehyde, 3,4-dimethylbenzaldehyde, 2,4-dimethylbenzaldehyde, and 2,5-dimethylbenzaldehyde, correspondingly. These reactions are synthesis reactions with very high reaction rates except the reaction of p-xylene with particularly low reactivity. In this case, BF$_3$ is used at a molar ratio of BF$_3$ to sum total of m-xylene and o-xylene in the feed xylene mixture of not more than 1.5, preferably 1.2-0.3. When BF$_3$ is used at a molar ratio of more than 1.5, ethylbenzene and partly p-xylene, if they are contained in the feed xylene mixture, undergo formylation. p-Ethylbenzaldehyde to be formed from ethylbenzene has a boiling point similar to that of 2,4-dimethylbenzaldehyde (B.P: 231° C. for the former, 233° C. for the latter) and thus is difficult to separate therefrom. That is, contamination by p-ethylbenzaldehyde considerably lowers the value as the raw material for trimellitic acid. However, in the present invention, even if the feed xylene mixture contains four isomers, i.e. ethylbenzene, o-xylene, m-xylene and p-xylene, the products are only 3,4-dimethylbenzaldehyde and 2,4-dimethylbenzaldehyde, while ethylbenzene and p-xylene remain as unreacted compounds without formylation.

The present invention is usually carried out in two steps; a step of mixing a feed xylene mixture with HF-BF$_3$ to form xylene-HF-BF$_3$ complex, and a step of formylating the xylene complex by pressurized CO.

For example, in the case of m-xylene (MZ), Complexing step:

Formylating step:

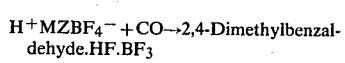

In the present invention, BF$_3$ is used at a molar ratio of not more than 1.5, preferably 0.3-1.2 to sum total of m-xylene and o-xylene in a feed xylene mixture. HF is used at a molar ratio of 3-8, preferably 4-6, to BF$_3$. If BF$_3$ is used at a molar ratio in excess of 1.5 to the sum total of m-xylene and o-xylene, ethylbenzene and p-xylene in the xylene mixture, particularly ethylbenzene with a high reactivity undergo formylation.

Other reaction conditions for the present invention are in accordance with the ordinary formylation reaction conditions. One example of the ordinary reaction conditions are, for example, a temperature of 0° C. and pressure of 3 kg/cm$^2$ gage for the complexing step and a temperature of 0° C. and a pressure of 10-20 kg/cm$^2$ gage for the formylation step. Reaction proceeds very rapidly in both steps.

In the complexing step, if a feed xylene mixture contains non-aromatic hydrocarbon, for example, paraffins of C$_8$-C$_{10}$, cycloparaffins, etc., or if a feed xylene mixture has a low m-xylene content, a uniform complex liquid phase may not be formed after reaction with HF-BF$_3$, and a light liquid phase containing non-aromatic hydrocarbon, ethylbenzene, p-xylene, etc. as main components may be formed. In that case, it is preferable to separate the light liquid phase from the complex phase in advance before carrying out the formylation and only the separated complex phase must be supplied to the formylation step. When a feed xylene contains ethylbenzene, 2-3% by weight of methylcyclopentane can be made present on the basis of ethylbenzene to suppress disproportionation reaction of ethylbenzene and effectively carry out formylation.

Formylation product solution is supplied to a decomposition column under benzene reflux to separate the product from HF—BF$_3$, where HF—BF$_3$ is vaporized and separated by heating. Recovered HF—BF$_3$ is recycled to the complexing step. Formylation product separated from HF—BF$_3$, that is, dimethylbenzaldehydes can be readily separated from unreacted xylenes by distillation. The unreacted xylenes are then effectively utilized as a feed for separating xylene isomers.

Effects of the present invention will be described below, referring to Examples.

EXAMPLES 1-5

A feed xylene mixture was subjected successively to complexing and formylation in a stainless steel autoclave having a net capacity of 2 l. The reaction product solution was subjected to gas chromatography after separation of HF—BF$_3$ therefrom, and the reaction product solution can be readily separated into unreacted xylenes and formylation products by distillation.

Feed composition, reaction conditions and results of Examples 1-5 are shown in the following Table.

TABLE

| | Ex. 1 | Ex. 2 | Ex. 3 | Ex. 4 | Ex. 5 |
|---|---|---|---|---|---|
| Feed | Mixed xylene | Mixed xylene | Xylene mixture from intermediate step of xylene separation (I) | Xylene mixture from intermediate step of xylene separation (II) | Xylene mixture from intermediate step of xylene separation (III) |
| Feed composition (Mol %) | | | | | |
| Non-aromatic hydrocarbon | 0.5 | 0.5 | 14.1 | 0 | 1.0 |
| Ethylbenzene | 19.9 | 19.9 | 16.5 | 0 | 32.0 |
| o-xylene | 19.1 | 19.1 | 15.6 | 0 | 31.5 |
| m-xylene | 40.7 | 40.7 | 36.7 | 80.0 | 0 |
| p-xylene | 19.8 | 19.8 | 17.1 | 20.0 | 35.5 |
| Reaction conditions | | | | | |
| Catalyst ratio by mole  BF$_3$/(m-xylene + o-xylene) | 0.50 | 1.0 | 0.9 | 1.2 | 0.8 |
| BF$_3$/HF | 0.23 | 0.23 | 0.21 | 0.25 | 0.20 |
| Complexing temperature (°C.) | 0 | −5 | −10 | 5 | −15 |
| Formylation temperature (°C.) | 0 | −5 | −5 | 0 | −15 |
| Formylation pressure (Kg/cm$^2$ gage) | 15 | 15 | 15 | 15 | 20 |
| Formylation time (minutes) | 20 | 20 | 20 | 20 | 20 |
| Results (mol %) | | | | | |
| Non-aromatic hydrocarbon | 0.5 | 0.5 | 14.1 | 0 | 1.0 |
| Ethylbenzene | 19.8 | 19.7 | 16.3 | 0 | 31.4 |
| o-xylene | 16.6 | 8.6 | 10.0 | 0 | 18.4 |
| m-xylene | 25.6 | 9.2 | 12.6 | 21.2 | 0 |
| p-xylene | 19.6 | 19.3 | 16.6 | 19.8 | 34.2 |
| Ethylbenzaldehyde | 0.1 | 0.2 | 0.2 | 0 | 0.6 |
| 3,4-dimethylbenzaldehyde | 2.5 | 10.5 | 5.5 | 0 | 13.0 |
| 2,4-dimethylbenzaldehyde | 15.1 | 31.3 | 24.0 | 58.5 | 0 |
| 2,5-dimethylbenzaldehyde | 0.2 | 0.5 | 0.5 | 0.2 | 1.3 |
| Other dimethylbenzaldehydes | Trace | 0.2 | 0.2 | 0.3 | 0.1 |

What is claimed is:

1. A process for formylating a xylene mixture containing at least m-xylene, o-xylene, and ethylbenzene by carbon monoxide in the presence of hydrogen fluoride and boron trifluoride as a catalyst wherein the hydrogen fluoride is used at a molar ratio of 3-8 to the boron trifluoride, which comprises conducting formylation at a molar ratio of boron trifluoride to the sum total of m-xylene and o-xylene in the xylene mixture of not more than 1.5, thereby selectively and correspondingly producing at least 2,4-dimethylbenzaldehyde and 3,4-dimethylbenzaldehyde.

2. A process according to claim 1, wherein the boron trifluoride is used at a molar ratio of 0.3-1.2 to sum total of m-xylene and o-xylene in the xylene mixture.

3. A process according to claim 1, wherein the hydrogen fluoride is used at a molar ratio of 4-6 to the boron trifluoride.

* * * * *